United States Patent [19]
Pietrafitta

[11] Patent Number: 5,295,952
[45] Date of Patent: Mar. 22, 1994

[54] SWAB FOR LAPAROSCOPY

[75] Inventor: Joseph J. Pietrafitta, Minnetonka, Minn.

[73] Assignee: Surgical Innovations, Inc., Minneapolis, Minn.

[21] Appl. No.: 717,292

[22] Filed: Jun. 19, 1991

[51] Int. Cl.⁵ .................. A61M 35/00; A61F 13/20
[52] U.S. Cl. ........................... 604/1; 604/15; 604/18
[58] Field of Search ........................ 604/1-3, 604/15, 18

[56] References Cited

U.S. PATENT DOCUMENTS

| | | | |
|---|---|---|---|
| 545,102 | 8/1895 | Sleem | 604/15 |
| 716,040 | 12/1902 | Holt | 604/15 |
| 726,460 | 4/1903 | Reid | 604/15 |
| 1,537,257 | 5/1925 | Mizner | 604/15 X |
| 1,794,221 | 2/1931 | Washburn et al. | 604/15 |
| 1,908,403 | 5/1933 | Budde | 604/15 X |
| 3,495,917 | 2/1970 | Truhan | 604/2 X |
| 3,595,233 | 7/1971 | Fuchslocher et al. | 604/15 |
| 3,890,954 | 6/1975 | Greenspan | 604/1 X |
| 3,983,868 | 10/1976 | Ring | 604/15 |
| 4,592,740 | 6/1986 | Mahruki | 604/15 |
| 4,620,534 | 11/1986 | Zartman | 604/15 X |
| 4,747,719 | 5/1988 | Parkin | 604/3 X |
| 4,749,655 | 6/1988 | Monthony et al. | 604/1 X |
| 4,854,760 | 8/1989 | Pike et al. | 604/3 X |
| 5,000,193 | 3/1991 | Heelis et al. | 604/1 |

OTHER PUBLICATIONS

"Endoscopic Kittner Blunt Dissecting Instrument", copyright 1991, by O. R. Concepts, Inc.

Primary Examiner—Randall L. Green
Assistant Examiner—Elizabeth M. Burke
Attorney, Agent, or Firm—Dorsey & Whitney

[57] ABSTRACT

In accordance with the present invention, a swab for use in laparoscopy is provided. The swab comprises an outer, generally tubular shank with a handle or gripping end and a working end. An inner shaft is slidably received in the shank and has a working end and a gripping end. A changeable, disposable absorbent tip is operably connected to the working end of the shaft. The swab includes a biasing means at the gripping ends of the shank and shaft for urging the absorbent tip toward the gripping ends.

5 Claims, 3 Drawing Sheets

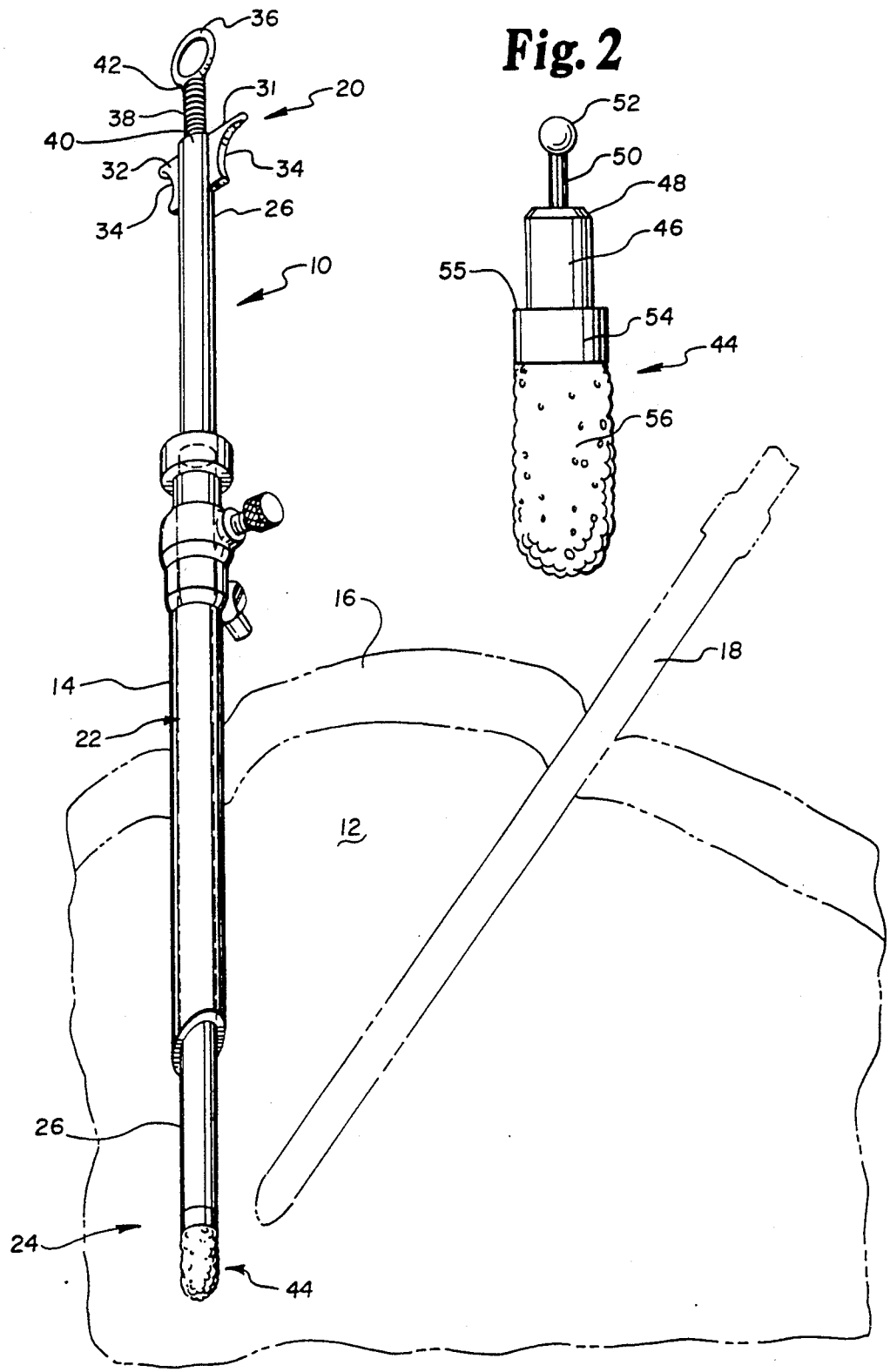

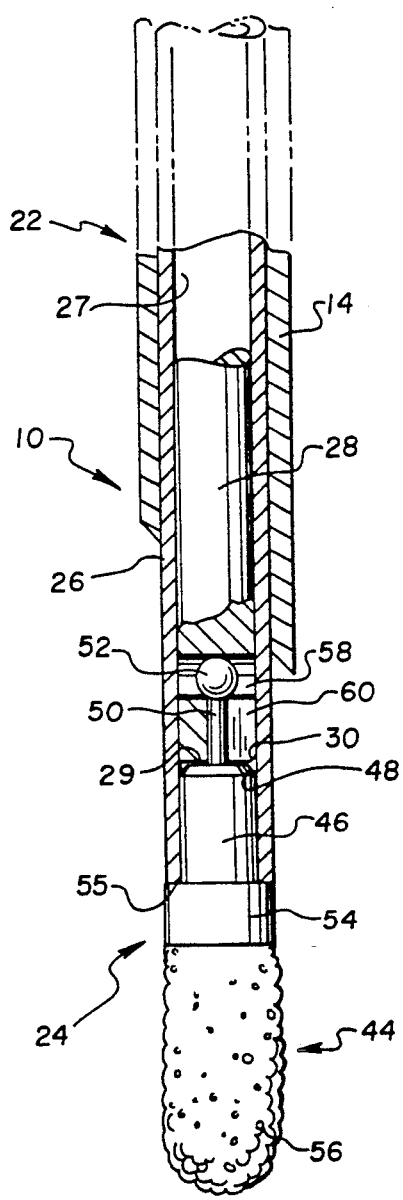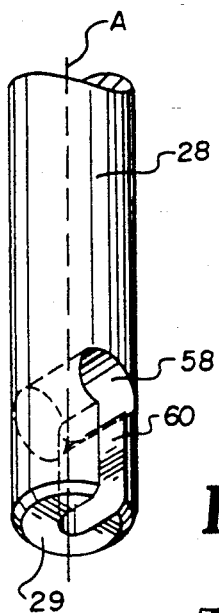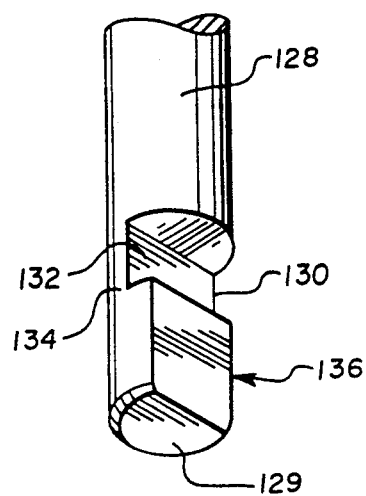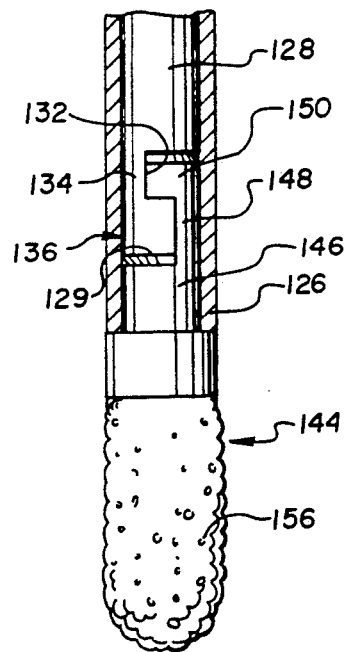

SWAB FOR LAPAROSCOPY

TECHNICAL FIELD

This invention relates generally to surgical instruments. In particular, it relates to a surgical instrument for use in laparoscopy wherein the instrument may be used intra-abdominally for absorbing fluid, palpating or cleansing tissues, applying therapeutic material or sampling during the surgical procedure.

BACKGROUND OF THE INVENTION

Laparoscopy is a form of surgery that involves visualizing the interior of the abdominal cavity using an illuminating optical instrument, a laparoscope. The laparoscope and other instruments are introduced into the abdominal cavity through puncture orifices in the abdominal wall.

Laparoscopic procedures are commenced by using a device known as a trocar. The trocar comprises a cannula or trocar sleeve (a hollow sheath or sleeve with a central lumen) and an obturator. The obturator is a solid metal rod with an extremely sharp three-cornered tip and is received in the cannula. The trocar is used to penetrate the abdominal wall, and the obturator is withdrawn from the cannula after the intra-abdominal end of the trocar is in the abdominal cavity. The cannula remains in the body wall throughout the surgical procedure and instruments used during laparoscopic procedures are introduced into the abdomen through it. Trocars, including cannulae, are available in different sizes to accommodate various surgical needs.

Laparoscopy traditionally has been used almost exclusively for gynecological surgery, but physicians specializing in other fields have begun to recognize the diagnostic and operative value of such procedures. The advantages of laparoscopic surgery include: procedures may be performed on an outpatient basis; surgeons are given the opportunity to view intra-abdominal viscera without performing a laparotomy, a large incision of the abdominal wall; small puncture wounds are created rather than large incisions, lessening trauma; incision sites for laparotomies may be determined; patient and insurer medical costs are reduced by shorter hospital stays; and postoperative patient discomfort, with recovery times measured in days as opposed to weeks, is lessened. As these advantages are being perceived, the number and variety of laparoscopic procedures being performed is increasing.

There is substantial interest in and need for providing task specific surgical instruments particularly adapted to general and neurological surgical procedures now being performed laparoscopically. Because laparoscopy is an evolving specialty within the field of general surgery, currently available instruments inadequately meet the needs of laparoscopic surgeons.

Absorbent materials, instruments having an associated absorbent structure or instruments for grasping and manipulating absorbent materials are used frequently in surgical procedures. Gauze, fabrics, cotton, sponges, and other synthetic or natural materials are representative of the absorbent materials. With regard to instruments used in conjunction with such materials, examples include hemostats, tweezers or rod-like instruments having a slot or other absorbent material receiving structure near one end. Such materials and instruments may be used for cleansing cavities, applying therapeutic materials, absorbing fluids, and sampling.

The superficial use of absorbent materials and instruments for handling them is well known. They may be used with ease in the body of a patient through the relatively large incisions made during typical general surgical procedures. Clearly, however, absorbents cannot be used in the typical fashion in laparoscopic procedures because any absorbent or instrument intended for intra-abdominal use must be introduced into the abdominal cavity through a cannula, as outlined above.

Elongated swabs, generally comprising a slender rod with an absorbent material carried at one end, are known. Urethral swabs provide one example. However, even this type of swab would present difficulties if use in laparoscopic procedures was attempted. One problem is that the absorbent material carried at the end of a swab may be separated from the rod to which it is attached. If this occurs in a body cavity opened by a relatively large incision, it is not difficult to retrieve the absorbent material from the body cavity through the incision. In laparascopy, when working exclusively through a cannula of relatively small diameter, the level of difficulty of retrieving a bit of absorbent material is multiplied many times.

Another problem with trying to use or adapt existing swabs for use in laparoscopic use is that it is difficult and time consuming to present a sterile absorbent material into the body cavity, because it is difficult to grip or attach a piece of absorbent material to the rod of existing swab or swab-type instruments.

Further complications are that the typical absorbent materials and instruments for handling them are impossible or difficult to insert into a cannula. Even if such materials and instruments are able to be inserted, they may become lodged or caught on portions of the cannula, and they will be extremely difficult to withdraw from the abdominal cavity through the cannula, particularly if the size or volume of the absorbent material is expanded by the absorption of fluids. Additionally, using known absorptive materials and instruments intra-abdominally may interfere with the surgeon's field of vision.

Clearly there are many problems unaddressed by currently available absorbent instruments for use during laparascopy. Accordingly, there is a need for a safe, inexpensive, efficient, semi-disposable swab for use in laparoscopy.

SUMMARY OF THE INVENTION

In accordance with the present invention, a swab for use in laparoscopy is provided. The swab comprises an outer, generally tubular shank with a handle or gripping end and a working end. An inner shaft is slidably received in the shank and has a working end and a gripping end. A changeable, disposable absorbent tip is operably connected to the working end of the shaft. The swab includes a biasing means at the gripping ends of the shank and shaft for urging the absorbent tip toward the gripping ends.

An object of the present invention is to provide a swab for use in laparoscopic surgical procedures wherein the swab carries a disposable absorbent tip that may be introduced into the abdominal cavity through a cannula to absorb fluids, to clean, dry or manipulate delicate tissue, to apply therapeutic materials, or for sampling.

Another object of the present invention is to provide a semi-disposable swab for use in laparoscopy wherein the handle of the instrument may be sterilized in an autoclave and carries a disposable, changeable absorbent tip. The instrument may be inserted easily into the abdominal cavity through a cannula, used intra-abdominally with confidence because the tip is securely connected to the handle, and may be withdrawn easily from the abdominal cavity through the cannula.

Yet another object of the present invention is to provide a semi-disposable swab for use in laparoscopy wherein the disposable portion, the absorbent material and supporting structure for that material at the intra-abdominal end or tip of the swab, may be replaced quickly and easily without jeopardizing a sterile operating field.

Yet a further object of the present invention is to provide an easily operated, safe, inexpensive, efficient swab, including an interchangeable variety of absorbent tips for connection to the swab, wherein the user may select an absorbent tip having desired qualities.

An important advantage of the present invention is that it combines ease of use while maximizing safety. The surgeon, an assisting physical or a nurse may rapidly attach a disposable absorbent tip to the handle of the swab, and the swab may be inserted easily through a cannula into the abdominal cavity. The surgeon can manipulate the swab with confidence, knowing that the absorbent tip will not be dislodged from the swab. After use, the swab easily may be withdrawn from the abdominal cavity through the cannula and the absorbent tip may be changed.

Other objects and advantages of the present invention will become more fully apparent and understood with reference to the following specification and to the appended drawings and claims.

BRIEF DESCRIPTION OF THE DRAWINGS

FIG. 1 is a perspective view of the present invention positioned, in a cannula, in the abdominal cavity of a patient. The abdominal wall is depicted by phantom lines.

FIG. 2 is a side elevational view of an absorbent tip for use with the present invention.

FIG. 3 is a fragmentary side elevational view of the present invention with parts cut away for clarity.

FIG. 4 is a fragmentary perspective detail depicting the end of the swab at which an absorbent tip is carried.

FIG. 5 is a fragmentary side elevational view of a modified form of the swab of the present invention.

FIG. 6 is a fragmentary perspective view of the modified form of the swab, depicting the end at which an absorbent tip is carried.

DETAILED DESCRIPTION OF THE PREFERRED EMBODIMENT

Figure 7:
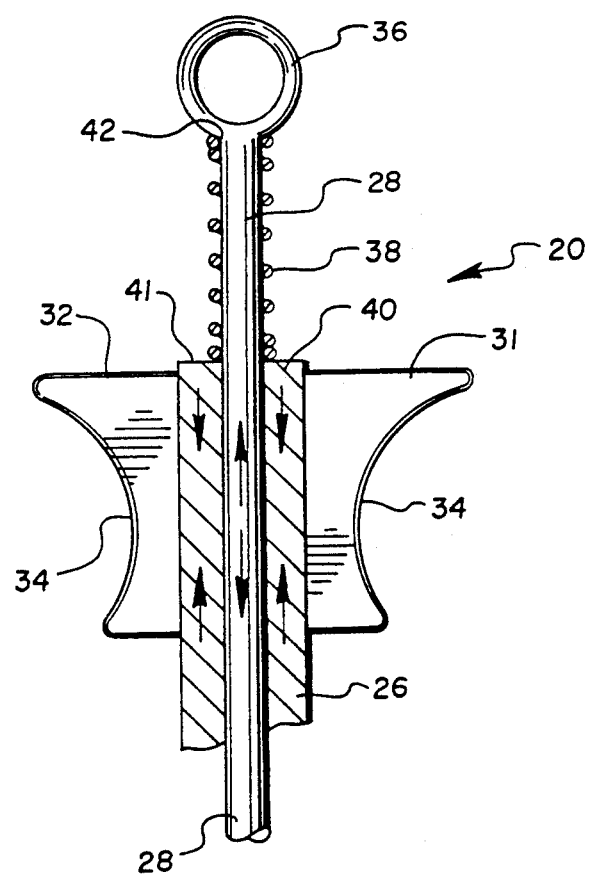
FIG. 7 is a fragmentary side elevational view of the handle end of the swab, with parts broken away for clarity.

The swab 10 in accordance with the present invention is depicted in FIG. 1 disposed in the intra-abdominal space 12 of a patient. A cannula 14 inserted through the abdominal wall 16 provides a pathway for the swab 10 or other laparoscopic instruments (not shown) to be inserted into the intra-abdominal space 12. An auxiliary cannula 18, depicted in phantom in FIG. 1, may be used for the insertion of additional instruments. The swab 10 of the present invention is depicted in the cannula 14 and broadly includes a hand grip end 20, an elongated, generally cylindrical shank 22, and a working end 24. Although not depicted, the shank portion 22 of the swab 10 may include indicia along the length of the shank 22 for indicating, for example, the depth of insertion of the swab 10, its proximity to tissue, or the size of visceral organs.

Referring to FIGS. 1 and 3, the shank 22 of the swab 10 includes an outer, elongated, generally tubular and cylindrical shank 26 having a hollow central core or lumen 27. A solid, elongated, generally cylindrical plunger shaft 28 is reciprocally and rotatably movable within the outer shank 26. The shaft 28 is generally coaxial with the shank 26 and has an outer diameter substantially equal to the inner diameter of the outer shank 26 and, specifically, the diameter of the lumen 27. The terminal, free end 29 of the shaft 28 has a bevel or chamfer 30.

Referring to FIGS. 1 and 7, the hand grippable handle end 20 of the swab includes a pair of thin, flat bilateral flanges 31, 32 attached to the outer shank 26. The flanges 31, 32 have arcuate finger receiving notches 34 and are coplanar, being connected to the outer shank 26 at 180° from each other. The handle end 20 also includes a finger ring 36 connected to the shaft 28. The finger ring 36 may be integral with the shaft 28 or it may be secured to the handle end of the shaft 28 in a suitable fashion. A compression spring 38 encircles the shaft 28 and extends between the finger ring 36 and the terminal end 40 of the tubular shank 26. The end 40 of the tubular shank 26 provides, or may be adapted further to provide, a shoulder or seating surface 41 for receiving one end of the spring 38. Likewise, the base area 42 of the finger ring 36 provides, or may be adapted to provide, a spring receiving seat (not shown).

Referring to FIGS. 2 and 3, the working end 24 of the swab 10 includes a changeable, disposable absorbent tip 44. The tip 44 includes a generally cylindrical, barrel-like body 46 having a bevel or chamfer 48 at one end. The body 46 may be solid or hollow. A generally round, thin, elongated neck 50 extends outwardly away from the body 46. An engagement ball or sphere 52 is attached at the terminal end of neck 50. At the opposite end of the body 46, a collar 54 is provided. The collar 54 may be formed integrally with the body 46 or it may be affixed to the body 46 by appropriate means. The collar 54 has an outer diameter that is substantially equal to the outer diameter of the shank 26. A flat collar shoulder 55 is adjacent the body 46. An appropriate absorbent material 56, including porous rubber, celllose, gauze or other suitable material, is attached to the collar 54 by hot pressing, adhesives or other suitable means. The diameter of the material 56 is preferably substantially equal to or slightly less than the diameter of the collar 54.

Referring to FIG. 4, the shaft 28 of the swab 10 carries the absorbent interchangeable and disposable tips 44. Specifically, adjacent the working terminal, free end 29 of the shaft 28, opposite the end with the finger ring 36, the shaft 28 includes a transverse bore or hole 58 for receiving the engagement sphere 52. A path 60 extends along the longitudinal axis (represented by line A) of the shaft 28 from the hole to the free, terminal end 29 of the shaft 28. The path 60 extends from the outer diameter of the shaft to adjacent the central longitudinal axis and, thus, is approximately the depth of a radius of the shaft 28. The innermost portion of the path 60 is rounded to compliment the generally round neck 50, but may be adapted to compliment necks having other shapes as well.

FIG. 3 depicts a tip 44 installed on the swab 10 and how the tip 44 is carried by the swab 10. The sphere 52 and the neck 50 of the tip 44 are received in the hole 58 and path 60 of the shaft 28, respectively. The generally flat, beveled end of the body 46 is held in closely adjacent relation to the terminal end 29 of the shaft 28 and may be in frictional contact therewith. Further reference to FIG. 3 shows that the outer diameter of the body 46 closely corresponds to the diameter of the lumen 27 of the outer shank 26. The open and free end of the outer shank 26 abuts the collar shoulder area 55 of the collar 54. It should be appreciated that the compression spring 38 (see FIGS. 1 and 7) urges the shaft 28 and the tip 44 in the direction of the handle end 20 to the position depicted in FIG. 3, thus locking the tip 44 into the relationship with the shaft 28 depicted in FIG. 3, wherein the free end of the shank 26 abuts the collar shoulder 55. Because the outer shank 26 is a continuous, generally cylindrical tube, there is no way for the tip 44 to become dislodged from the swab 10 except by manipulation of the handle end 20 and, specifically, exerting against the force of the spring 38 an axial force on the shaft 28 sufficient to reciprocally move the shaft 28 in the outer shank 26 until the absorbent tip 44, including the engagement sphere 52, is removed entirely from within the outer shank 26.

Referring to FIGS. 5 and 6, a modified form the swab 10 of the present invention is depicted. The modified form will be numbered substantially in common with the preferred embodiment, however a one (1) will be added to each numerically-identified portion of the modified form. Specifically, a shaft notch 130 is cut adjacent the terminal, free end 129 of the shaft 128. The plane of the flat back wall 132 at the innermost portion of the notch 130 is adjacent the central longitudinal axis of the shaft 128 and forms a neck 134. Between the notch 130 and the terminal end 129 of the shaft 128, the body of the shaft 128 is relieved to form a shaft hook 136. FIG. 5 reveals how the tip 44 (FIG. 4) is modified to conform with the modified shaft 128 depicted in FIG. 6. Specifically, the body 146 of the tip 144 includes a neck 148 and a tip hook 150. The shaft hook 136 and the tip neck 148 are complimentary whereby, when parallel and closely adjacent or in contact, the two are substantially equal to the diameter of the shaft 128. Likewise, the shaft neck 134 and the tip hook 150 are complimentary and have a similar relationship. As in the preferred embodiment, the body 146, and absorbent 156 carried thereby, has an outer diameter which is substantially equal to the inner diameter of the tubular outer shank 126.

In use, a surgeon or an assistant holds the swab 10 at the hand grippable handle end 20, placing the fingers or the thumb and fingers of the gripping hand in the finger notches 34 of the flanges 31, 32. The thumb or another finger may be received in the finger ring 36 and, held in this fashion with one hand, the shaft 28 may be reciprocally or slidably moved with respect to the outer tubular shank 26 against the bias of the compression spring 38. The movement of the shaft 28 causes the terminal end 29 to extend from or retract toward the end of the outer shank 26 at the working end 24 of the swab 10, exposing or covering the hole 58. The hole 58 is exposed when the shaft 28 is extended sufficiently. A pre-packaged, disposable sterile absorbent tip 44 is connected to the shaft 28 by moving the engagement sphere 52 into the hole 58; the neck 50 will follow into the path 60. Pressure on the finger ring 36 against the compression spring 38 may be released. The spring 38 biases the working end 24 of the shaft 28 toward the handle end 20, drawing the terminal end 29 of the shaft 28, and a portion of the tip 44 carried at that end 29, into the outer shank 26 until the shoulder 55 of the collar 54 come into contact with the annular end of the outer shank 26. In this position, depicted in FIG. 3, the absorbent tip 44 is releasably, yet non-removably and rigidly attached and cannot be disloged from the swab 10.

The swab 10, with the tip 44 in place, may be inserted through the cannula 14 as depicted in FIG. 1. The surgeon may use the absorbent tip 44 of the swab 10 in the abdominal cavity 12 with confidence that the tip 44 will not be dislodged from the swab 10. Following use, the swab 10 may be withdrawn through the cannula 14, the finger ring 36 may be depressed, and the used absorbent tip 44 may be quickly and easily released from the swab 10. A replacement absorbent tip 44 may then be attached as outlined above; use may be repeated as many times as necessary.

A number of variations of the present invention can be made. For example, the length and diameter of the swab 10 may be varied as long as the limiting factors of the length and diameter of cannulae are met. Representative cannula diameters are 3,5 and 10 millimeters. Although a generally cylindrical, slightly conical absorbent material 56 is depicted for the absorbent tip 44, other configurations might be used as well. The material of the swab 10, other than the absorbent material 56 at the tip 44, is typically stainless steel or stainless steel alloys, but other appropriate materials such as other metallic alloys, thermoplastic or fiberglass might be used as long as they are sufficiently rigid and strong upon curing. When a plastic is used to form the swab 10 or a portion thereof, the entire swab 10 or the plastic parts may be sterilized for reuse in the same or another procedure by gas autoclaving. Alternatively, the entire swab 10 of the present invention might be disposable after a single use or procedure. The swab 10 might be used with other special purpose tips in addition to absorbent tips 44. For example, the body 46 of the tip 44 might be adapted to carry sampling devices or probe devices.

The swab 10 of the present invention may be used in laparoscopy for cleansing a cavity, absorbing liquids, applying therapeutic materials or for sampling. It is easily inserted through cannulae, minimizes interference with the users' field of view, and may be used with confidence intra-abdominally because the tip 44 carried by the swab 10 may be securely locked in place. The swab 10 may be withdrawn through the cannula easily after use and the inter-changeable tips 44 (or 144) may be replaced quickly and conveniently by other tips 44.

It is contemplated that various changes, including those mentioned above, can be made without deviating from the spirit of the present invention. It is therefore desired that the foregoing description be considered as illustrative, not restrictive and that reference be made to the appended claims to indicate the scope of the invention.

What is claimed is:

1. A swab comprising:
    a substantially cylindrical, straight outer hollow shank with a shank handle end and a shank working end;

a rigid shaft movably received in said shank, said shaft having a shaft handle end generally aligned with the shank handle end and a shaft working end generally aligned with said shank working end;

absorbent tip means for absorbing, said absorbent tip means operably and removably carried at the shaft working end and including generally opposed first and second ends and a body extending between said first and second ends, said body having a cross-sectional area, said first end carrying an absorbent material, a neck extending from said second end of said body, said neck having a terminal end and a central portion having a cross-sectional area that is less than the cross-sectional area of said body;

a spring for constantly urging said absorbent tip means toward said shank handle end, said spring operably coupled between said shank and said shaft; and connecting means for operably connecting said absorbent tip means to said shaft, said connecting means comprising:

a transverse opening in said shaft adjacent to the shaft working end and a cut away extending between said opening and said shaft working end, said opening for being aligned with and receiving said terminal end and said cut away area for being aligned with said central portion.

2. The swab according to claim 1, wherein said central portion and said terminal end of the neck are complementary to said cut away and said transverse opening, respectively.

3. The swab according to claim 2, wherein said shank has a lumen with a cross-sectional area closely corresponding to said cross-sectional area of said body, whereby said body may be drawn into said lumen and fits snugly and removably therein.

4. The swab according to claim 3, wherein when said absorbent tip means is being carried by said shaft, the total cross-sectional area of said complementary central portion and cut away area is substantially equal to the cross-sectional area of said body.

5. The swab according to claim 4, wherein said spring is a coil spring operably coupled between said shank and said shaft adjacent to said shank and shaft handle ends.

* * * * *